United States Patent [19]

Hanafin

[11] Patent Number: 4,629,791
[45] Date of Patent: Dec. 16, 1986

[54] NOVEL 3-HALO-2-HYDROXYALKYL CARBAMATES

[75] Inventor: Joseph W. Hanafin, Framingham, Mass.

[73] Assignee: The Dow Chemical Company, Midland, Mich.

[21] Appl. No.: 639,174

[22] Filed: Aug. 9, 1984

[51] Int. Cl.$^4$ ............................................. C07C 125/06
[52] U.S. Cl. .................................. 544/387; 544/388; 544/398
[58] Field of Search ....................... 544/398, 388, 387; 260/453 R

[56] References Cited

U.S. PATENT DOCUMENTS

| | | | |
|---|---|---|---|
| 2,830,038 | 4/1958 | Pattison | 528/49 |
| 3,072,613 | 1/1963 | Whelan, Jr. et al. | 528/211 |
| 3,440,230 | 4/1969 | Doss | 528/369 |
| 3,445,436 | 5/1969 | Lake et al. | 528/49 |
| 3,484,413 | 12/1969 | Kaufman | 528/49 |
| 3,624,016 | 11/1971 | Lew | 428/260 |
| 3,684,429 | 8/1972 | Tesoro et al. | 8/129.6 |
| 3,692,729 | 9/1972 | Kolbel et al. | 526/273 |
| 3,849,230 | 11/1974 | Breslow | 156/30 |
| 3,872,097 | 3/1975 | Habermeier et al. | 548/310 |

OTHER PUBLICATIONS

El-Giamal, *Mokromolecular Chem.*, 177, 2259 (1976).

Farrissey et al., *J. Heterocyclic Chem.*, 7, 331 (1970).

*Primary Examiner*—John Kight
*Assistant Examiner*—M. L. Moore
*Attorney, Agent, or Firm*—Norman L. Sims

[57] ABSTRACT

The invention is a compound which comprises one or more 3-halo-2-hydroxyalkyl carbamate moieties; wherein the carbamate nitrogen is tertiary. In preferred embodiments, the carbamate nitrogen is tertiary, and the carbamate nitrogen is further substituted by an alicyclic or aliphatic moiety or is part of a heterocyclic ring, wherein the heterocyclic ring can contain an oxygen or sulfur atom or may contain another tertiary 3-halo-2-hydroxyalkyl carbamate moiety; or wherein two or more of such 3-halo-2-hydroxyalkyl carbamates are linked by an aliphatic or alicyclic moiety.

Another aspect of the invention is a process for the preparation of such 3-halo-2-hydroxyalkyl carbamates which comprises contacting an epihalohydrin carbonate with a secondary amine-containing compound, wherein the secondary amine has a pKa at which the secondary amine will react with the epihalohydrin carbonate and which does not catalyze the formation of unwanted by-products, in a polar organic solvent under conditions such that a 3-halo-2-hydroxyalkyl carbamate, wherein the carbamate nitrogen is tertiary, is prepared.

17 Claims, No Drawings

NOVEL 3-HALO-2-HYDROXYALKYL CARBAMATES

BACKGROUND OF THE INVENTION

This invention relates to novel 3-halo-2-hydroxyalkyl carbamates, and a process for the preparation thereof.

The novel 3-halo-2-hydroxyalkyl carbamates of this invention are useful in preparing 2,3-epoxyalkyl carbamates which are useful as reactive diluents, ultraviolet light stable epoxy resins, additives to reduce the brittleness of epoxy resins, and as cross-linking agents in epoxy resins, polyurethanes and epoxy novolak systems.

Doss, U.S. Pat. No. 3,440,230, discloses a process for the preparation of a carbamate in which a polyisocyanate is reacted with an epoxy alcohol so as to form a carbamate in which the carbamate nitrogen has an active hydrogen atom attached thereto. The reaction to form the carbamate may be represented by the following equation:

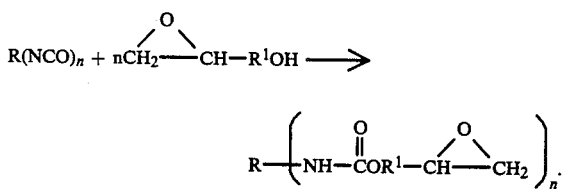

See also Kaufmann, U.S. Pat. No. 3,484,413 and Tesoro, U.S. Pat. No. 3,684,429. As described hereinbefore, the compounds made by this process result in a carbamate in which the carbamate nitrogen has an active hydrogen atom attached. Such compounds easily rearrange to prepare cyclic compounds, in particular, 4-hydroxymethyl-1,3-oxazolidin-2-ones. See U.S. Pat. No. 3,484,413 and Farrissey et al., *J. of Heterocyclic Chem.*, 7, 331 (1970). This formation of cyclic compounds is undesirable as such rearrangements result under conditions at which the epoxy carbamates would normally be used.

What are needed are stable 3-halo-2-hydroxyalkyl carbamates.

SUMMARY OF THE INVENTION

Another aspect of the invention is a process for the preparation of such 3-halo-2-hydroxyalkyl carbamates which comprises contacting an epihalohydrin carbonate with a secondary amine-containing compound, wherein the secondary amine has a pKa at which the secondary amine will react with the epihalohydrin carbonate and which does not catalyze the formation of unwanted by-products, in a polar organic solvent under conditions such that a 3-halo-2-hydroxyalkyl carbamate, wherein the carbamate nitrogen is tertiary, is prepared.

The novel 3-halo-2-hydroxyalkyl carbamates are surprisingly stable.

DETAILED DESCRIPTION OF THE INVENTION

Included among the 3-halo-2-hydroxyalkyl carbamates with tertiary carbamate nitrogen atoms are the 3-halo-2-hydroxyalkyl carbamates and poly-(3-halo-2-hydroxyalkyl)polycarbamates. Preferred 3-halo-2-hydroxyalkyl carbamates are 3-halo-2-hydroxyalkyl dialiphatic or dialicyclic carbamates and 3-halo-2-hydroxyalkyl cycloalkylene carbamates. Preferred poly-(3-halo-2-hydroxyalkyl)polycarbamates are poly-(3-halo-2-hydroxyalkyl)N-aliphatic or N-alicyclic alkylene polycarbamates, or bis-(3-halo-2-hydroxyalkyl)1,4-piperazinyl dicarboxylates. In one more preferred embodiment, the 3-halo-2-hydroxyalkyl carbamates with tertiary nitrogen atoms are the poly-(3-halo-2-hydroxyalkyl)N-aliphatic or N-alicyclic alkylene polycarbamates or the bis-(3-halo-2-hydroxyalkyl)1,4-piperazinyl dicarboxylates.

Of the 3-halo-2-hydroxyalkyl carbamates, the 3-halo-2-hydroxypropyl carbamates are more preferred, examples of which include 3-halo-2-hydroxypropyl dialiphatic or dialicyclic carbamates, 3-halo-2-hydroxypropyl cycloalkylene carbamates, poly-(3-halo-2-hydroxypropyl)N-aliphatic or N-alicyclic alkylene polycarbamates or bis-(3-halo-2-hydroxypropyl)1,4-piperazinyl dicarboxylates; of which poly-(3-halo-2-hydroxypropyl)N-aliphatic or N-alicyclic alkylene polycarbamates and bis-(3-halo-2-hydroxypropyl)1,4-piperazinyl dicarboxylates are even more preferred.

Among preferred 3-halo-2-hydroxyalkyl carbamates in this invention are those which correspond to the formulas

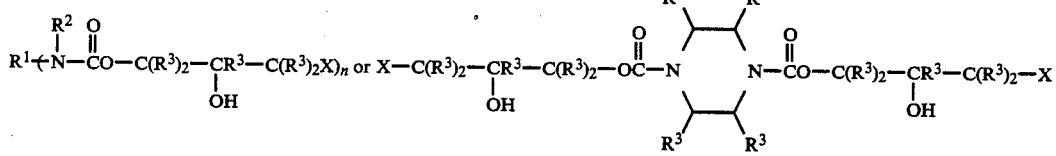

The invention is a compound which comprises one or more 3-halo-2-hydroxyalkyl carbamate moieties; wherein the carbamate nitrogen is tertiary. In preferred 3-halo-2-hydroxyalkyl carbamates, the carbamate nitrogen is tertiary, and the carbamate nitrogen is further substituted by an alicyclic or aliphatic moiety or is part of a heterocyclic ring, wherein the heterocyclic ring can contain an oxygen or sulfur atom or may contain another tertiary 3-halo-hydroxyalkyl carbamate moiety; or wherein two or more of such 3-halo-2-hydroxyalkyl carbamates are linked by an aliphatic or alicyclic moiety.

wherein
$R^1$ is separately in each occurrence an n valent aliphatic or cycloaliphatic hydrocarbon;
$R^2$ is separately in each occurrence an aliphatic or cycloaliphatic moiety;
$R^3$ is separately in each occurrence hydrogen or an aliphatic moiety;
X is Br, Cl or I; and
n is an integer of 1 to 6;
wherein $R^1$ and $R^2$ may be joined to form a cycloalkylene moiety which can contain the heteroatoms O, N or S.

Preferred 3-halo-2-hydroxyalkyl carbamates include the following: (1) a 3-halo-2-hydroxyalkyl dialiphatic or dialicyclic carbamate which corresponds to the formula

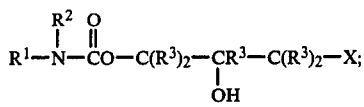

(2) a poly-(3-halo-2-hydroxyalkyl)N-aliphatic or N-alicyclic alkylene polycarbamate which corresponds to the formula

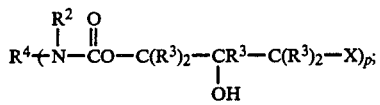

(3) a 3-halo-2-hydroxyalkyl cycloalkylene carbamate which corresponds to the formula

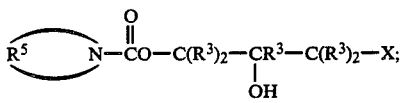

or (4) a bis-(3-halo-2-hydroxyalkyl)1,4-piperazinyl dicarboxylate which corresponds to the formula

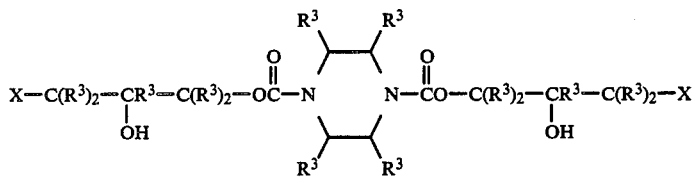

wherein
$R^1$ is separately in each occurrence an aliphatic or cycloaliphatic radical;
$R^2$ is separately in each occurrence an aliphatic or cycloaliphatic radical;
$R^3$ is separately in each occurrence hydrogen or an aliphatic radical;
$R^4$ is a p valent aliphatic or cycloaliphatic hydrocarbon;
$R^5$ is an alkylene radical, which can contain a heteroatom of O, S or N, which together with the carbamate nitrogen atom forms an aliphatic heterocyclic ring;
X is Cl, Br or I; and
p is an integer of between 2 and 6, inclusive.

In the hereinbefore-described formulas, $R^1$ is preferably a $C_{1-20}$ aliphatic or $C_{3-20}$ cycloaliphatic radical; more preferably a $C_{1-20}$ alkyl radical; and most preferably a $C_{1-10}$ alkyl radical. $R^2$ is preferably a $C_{1-20}$ aliphatic radical or a $C_{3-20}$ cycloaliphatic radical; more preferably a $C_{1-20}$ alkyl radical; and most preferably a $C_{1-10}$ alkyl radical. $R^3$ is preferably hydrogen or a $C_{1-20}$ aliphatic radical; more preferably hydrogen or a $C_{1-20}$ alkyl radical; even more preferably hydrogen or a $C_{1-3}$ alkyl radical; and most preferably hydrogen. $R^4$ is preferably a p-valent $C_{1-20}$ aliphatic or $C_{3-20}$ cycloaliphatic hydrocarbon radical; more preferably a p-valent $C_{1-20}$ alkyl radical; and most preferably a p-valent $C_{1-10}$ alkyl radical. The

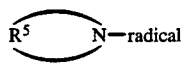

preferably forms a piperidine, pyrrolidine, oxazine, imidazolidine, morpholine, ethyleneamine, 3-pyrroline, or perhydro-1,3-thiazine ring; more preferably a piperidine, pyrrolidine, oxazine, or morpholine ring; and most preferably a pyrrolidine ring or piperidine ring. Preferably, n is between about 2 and 4, inclusive, and is most preferably 2. Preferably, p is between 2 and 4, inclusive, and is most preferably 2. X is preferably Cl or Br, and most preferably Cl.

The novel 3-halo-2-hydroxyalkyl carbamates of this invention are prepared by a process wherein an epihalohydrin carbonate is reacted with a secondary amine, which has a pKa at which the secondary amine will react with the epihalohydrin carbonate and will not catalyze the formation of unwanted by-products, to prepare a 3-halo-2-hydroxyalkyl carbamate wherein the carbamate nitrogen is a tertiary nitrogen atom, and the carbamate nitrogen is further substituted by an alicyclic or aliphatic moiety, or is part of a heterocyclic ring which can contain an oxygen or sulfur atom or may contain another tertiary 3-hydroxy-2-haloalkyl carbamate, or where 2 or more of such 3-hydroxy-2-haloalkyl carbamates are linked by an aliphatic or alicyclic moiety.

For use in this invention any epihalohydrin carbonate which will react with a secondary amine with a suitable pKa can be used in this process. Included among desirable epihalohydrin carbonates (4-(1-haloalkyl)dioxolan-2-ones) are those which correspond to the formula

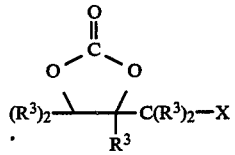

wherein $R^3$ is as defined hereinbefore and X is iodine, chlorine, or bromine. Examples of epihalohydrin carbonates include epiiodohydrin carbonate, epichlorohydrin carbonate and epibromohydrin carbonate. The preferred epihalohydrin carbonate is epichlorohydrin carbonate.

The amines useful in this invention include all secondary amines which have a pKa at which the amine reacts with an epihalohydrin carbonate and does not catalyze the formation of unwanted by-products. Secondary amines with pKa's which are too low will not react with epihalohydrin carbonates. Secondary amines with pKa's which are too high result in the formation of polymeric by-products. Preferred secondary amines are those with pKa's of between about 6 and 12. Desirable secondary amines include those which correspond to the formula

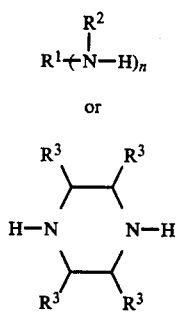

wherein $R^1$, $R^2$, $R^3$ and N are as hereinbefore defined.

Preferred secondary amines include aliphatic secondary amines which correspond to the formula

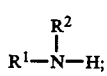

heterocyclic secondary amines which correspond to the formula

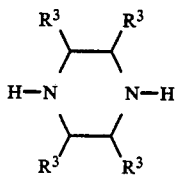

aliphatic secondary polyamines which correspond to the formula

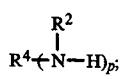

or piperazines which correspond to the formula

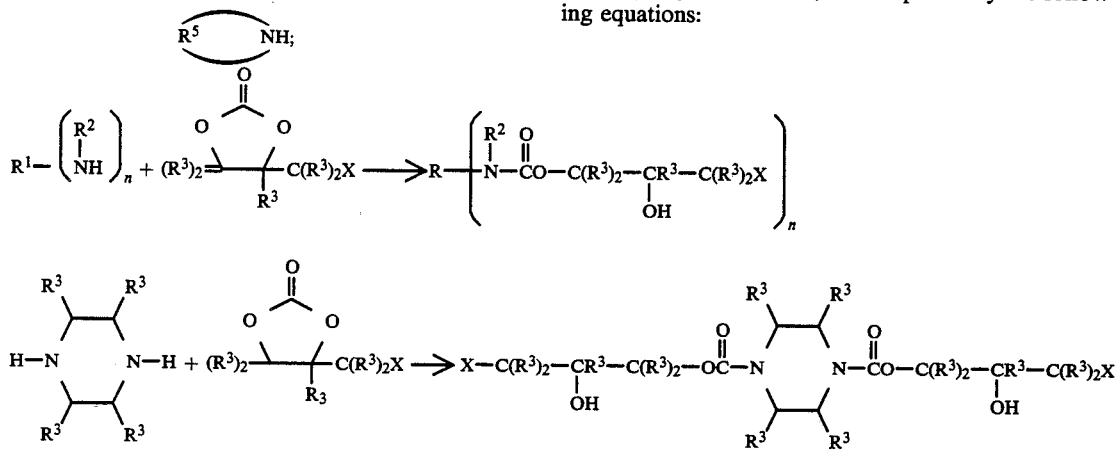

wherein $R^1$ is separately in each occurrence an aliphatic or cycloaliphatic radical;

$R^2$ is separately in each occurrence an aliphatic or cycloaliphatic radical;

$R^3$ is separately in each occurrence hydrogen or an aliphatic radical;

$R^4$ is a p valent aliphatic or cycloaliphatic hydrocarbon;

$R^5$ is an alkylene radical which can contain a heteroatom of O, S or N, which together with the nitrogen forms an aliphatic heterocyclic ring; and p is an integer between 2 and 6, inclusive.

It is more preferable that the secondary amines useful in this invention have a pKa of between 7.5 and 12. Among more preferred amines are the aliphatic secondary polyamines and piperazine.

Examples of secondary amines useful in this invention are dimethylamine, diethylamine, di-n-propylamine, diisopropylamine, di-n-butylamine, di-sec-butylamine, dipentylamines, dihexylamines, dioctylamines, ditriacontenylamine, N-methyl ethylamine, N-methyl propylamine, N-methyl octadecylamine, N-ethyl hexylamine, N-ethyl dodecylamine, N-propyl dodecylamine and the like.

Examples of heterocyclic aliphatic secondary amines include piperidine, pyrrole, imidazolidine, pyrazole, piperazine and the like.

The process for the preparation of the 3-halo-2-hydroxyalkyl carbamates, is exemplified by the following equations:

In the process for the preparation of the 3-halo-2-hydroxyalkyl carbamates the epihalohydrin carbonates are contacted with the secondary amines in an equivalent ratio of between about 0.01:1.0 and 100:1.0, preferably in an equivalent ratio of between about 20:1.0 and 1.0:1.0, and most preferably in an equivalent ratio of 2.0:1.0 and 1.0:1.0. An equivalent of amine means herein that amount of a secondary amine which will react with one mole of an epihalohydrin carbonate to give the desired 3-halo-2-hydroxyalkyl carbamate.

The secondary amine and epihalohydrin carbonate are contacted in a polar organic solvent. Examples of desirable polar organic solvents include acetonitrile, tetrahydrofuran, dioxane, and lower alkanols. Preferred solvents are the lower alkanols, with ethanol being the most preferred.

In general, the ratio of solvents to reactants is any ratio in which the reactants are dissolved. It is preferred that the weight ratio of solvent to epihalohydrin carbonate be 5.0:1.0 or greater.

The preparation of the 3-halo-2-hydroxyalkyl carbamates can proceed at any temperature at which the epihalohydrin carbonate reacts with the secondary amine. Preferable temperatures are between about 0° C. and 100° C., with between 20° C. and 50° C. being preferred. If the reaction is run below 0° C., excessively long reaction times are required, while at temperatures of greater than 100° C., side reactions, including the formation of the epoxide group followed by reaction with unreacted amine can lead to the formation of oligomers and by-products.

This process is usually carried out for a period of time sufficient for the amine to react completely with epihalohydrin carbonate and can vary from between about 5 minutes and 48 hours, dependent upon the amine temperature and solvent chosen. Preferred reaction times are between about 1 and 24 hours.

This process may be run at any pressure at which the reaction proceeds. Atmospheric pressure is preferred. It is preferable to run this reaction in an inert gas atmosphere, for example, under a nitrogen or argon atmosphere.

It is preferable to add an acid scavenger during this step. Compounds which form salts with hydrogen halide and are inert to the reactants are suitable. Examples of preferable acid scavengers are alkali metal bicarbonates and alkaline earth metal bicarbonates. More preferred acid scavengers are sodium and potassium bicarbonates. The acid scavengers react with any hydrogen halide formed during the process to prevent the formation of unwanted by-products due to the presence of the hydrogen halide. As a result, the product can be recovered in higher purity. A sufficient amount of acid scavenger to prevent the formation of by-products is suitable. Preferably the mole ratio of acid scavenger to amine is between about 0.05:1 and 5:1, more preferably between 1:1 and 3:1.

The 3-halo-2-hydroxyalkyl carbamates can be recovered and isolated by removing the solvent of the reaction mixture. The solvent can be removed by evaporation. Thereafter, the remainder which generally comprises the 3-halo-2-hydroxyalkyl carbamates and epihalohydrin carbonate is dissolved in a slightly polar solvent and passed through a silica adsorbent. A preferable solvent is a 50/50 mixture of chloroform (trichloromethane) and methylene chloride (dichloromethane). The 3-halo-2-hydroxyalkyl carbamate is adsorbed while the epihalohydrin carbonate passes through the adsorbent. The 3-halo-2-hydroxyalkyl carbamate can be desorbed from the silica by passing a desorbent through the adsorbent. Suitable desorbents are liquids which are strongly polar and dissolve the 3-halo-2-hydroxyalkyl carbamates. Preferred desorbents are the alkanols, with methanol or ethanol being most preferred. The desorbent can thereafter be evaporated away to leave the product.

Alternatively, the 3-halo-2-hydroxyalkyl carbamate can be recovered by removing the reaction solvent by evaporation, dissolving the concentrated reaction mixture in a chlorinated aliphatic hydrocarbon and washing the solution with a mildly acidic aqueous solution. Preferably, the aqueous solution contains less than 10 percent by weight of a protic acid, more preferably less than 5 percent by weight. A preferred protic acid is hydrochloric acid. A preferred solvent is methylene chloride.

The 3-halo-2-hydroxyalkyl carbamate so recovered can thereafter be used to prepare a 2,3-epoxyalkyl carbamate. It is not necessary to isolate the 3-halo-2-hydroxyalkyl carbamate to prepare a 2,3-epoxyalkyl carbamate provided the reaction solvent used to prepare 2,3-epoxyalkyl carbamate is a lower alkanol.

The 3-halo-2-hydroxyalkyl carbamates are converted to 2,3-epoxyalkyl carbamates by contacting the 3-halo-2-hydroxyalkyl carbamates with an alkali metal hydroxide, alkaline earth metal hydroxide, secondary or tertiary amine with a pH of 8.0 or greater, or a polymeric backbone with pendant moieties of hydroxide, secondary or tertiary amines with a pH of 8.0 or greater. This process step is exemplified by the following equations:

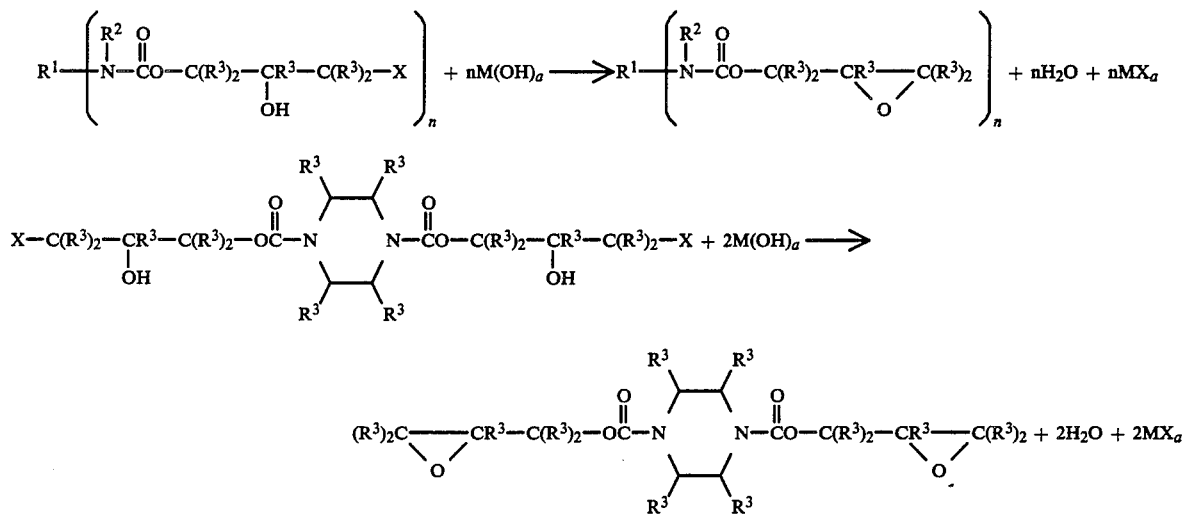

wherein $R^1$, $R^2$, $R^3$, X and n are as defined hereinbefore; a is 1 or 2; and M is an alkali metal or alkaline earth metal.

The alkali metal hydroxide, alkaline earth metal hydroxide, or secondary amine can be dissolved in the reaction mixture. Alternatively the amine, alkali metal hydroxide, or alkaline earth metal hydroxide can be supported in a manner such that they are pendant moieties from a polymeric backbone. An example of this is an ion-exchange resin wherein the amine or hydroxide moieties are pendant. Preferred are the alkali metal hydroxides, with the sodium hydroxide or potassium hydroxide being most preferred. The alkali metal hydroxides are preferably used in a powdered form.

The amines or hydroxides are contacted with the 3-halo-2-hydroxyalkyl carbamates in a manner such that there is at least one equivalent of amine or hydroxide per equivalent of 3-halo-2-hydroxyalkyl carbamate. Equivalent of 3-halo-2-hydroxyalkyl carbamate means herein that amount which will react with one mole of hydroxide moieties. The equivalent ratio of hydroxides or amines to the 3-halo-2-hydroxyalkyl carbamates is preferably between about 1:1 and 5:1, more preferably between about 1:1 and 2:1.

The reactants are contacted in a lower alkanolic solvent. Examples of lower alkanolic solvents are methanol, ethanol, propanol, butanol and pentanol. The preferred solvent is ethanol. In general, the ratio of solvent to reactants is not critical and any amount which allows the reaction to proceed is suitable. Preferably, the ratio of solvent to 3-halo-2-hydroxyalkyl carbamate is between about 10:1 and 1:1, more preferably between about 5:1 and 1:1.

This reaction step can take place at any temperature at which the reaction proceeds. Preferable temperatures are between about 0° C. and 50° C., with between about 0° C. and 20° C. being most preferred.

The process can be run at any pressure at which the reaction proceeds. Atmospheric pressure is preferred. It is preferable to run the reaction under an inert atmosphere, for example, under a nitrogen or argon atmosphere.

The by-products of this process are water and the halide salt of the amine, the alkali metal or alkaline earth metal. This salt may be removed by adding an ether to the reaction solution either after the reaction has been completed or before the reaction is initiated. In the embodiment wherein the ether is added prior to the reaction initiation, the salt will precipitate as it is formed. Suitable ethers are the dialkyl ethers such as dimethyl ether, diethyl ether, and the like.

The 2,3-epoxyalkyl carbamates can be recovered by filtering off the amine salt, alkali metal salt or alkaline earth metal salt, and thereafter distilling away the solvent and ether. The product can then be taken up in a chlorinated hydrocarbon solvent and contacted with a mild acid, a 2-5 percent concentration of any protic acid, for example, hydrochloric acid. The organic layer can thereafter be dried over a dessicant, the solvent stripped off to leave the product which crystallizes upon standing.

The 2,3-epoxyalkyl carbamates can be used to prepare polyepoxides and cured epoxy resins.

SPECIFIC EMBODIMENTS

The following examples are presented to further illustrate the invention and do not limit the scope of the invention or claims. All parts and percentages are by weight unless otherwise specified.

EXAMPLE 1

Prepartion of (2,3-epoxypropyl) piperidine N-carboxylate

To a stirred solution of epichlorohydrin carbonate (6.8 g, 0.05 mole) in 25 ml of absolute methanol in a 100-ml round-bottom flask at room temperature is added piperidine (4.25 g, 0.05 mole) in 10 ml of absolute methanol over 15 minutes. The solution is then heated to 50° C. for 2 hours. Analysis by gas chromatography and infrared spectra shows only carbonyl absorption at 1690–1710 cm$^{-1}$ due to the urethane linkage and no trace of unreacted starting materials.

The solution is cooled in an ice bath to 10° C. and powdered NaOH (2.0 g, 0.05 mole) is added. The solution immediately becomes cloudy as insoluble NaCl forms. After 10 minutes, a gas chromatographic trace shows no open chain intermediate chlorohydrin. The solution is filtered, the solid NaCl is washed with 20 ml of methanol and the combined organic fractions are stripped of solvent on a rotary evaporator leaving a light tan-colored oil of moderate viscosity (9.2 g, 99 percent). A nuclear magnetic resonance spectrum (CDCl$_3$) of this oil indicates it to be the desired 2,3-epoxypropyl 1,4-piperidinyl carboxylate.

The crude oil distills at 105° C. (0.4 mm Hg pressure) to give a water white liquid product of more than 99 percent purity.

EXAMPLE 2

Preparation of N,N-dimethyl-2,3-epoxypropyl Carbamate

To a stirred solution of epichlorohydrin carbonate (6.8 g, 0.05 mole) in 40 ml of ethanol at room temperature is added a 40 weight percent aqueous solution of dimethylamine (5.625 g solution eq. to 2.25 g, 0.05 mole) through an addition funnel. The rate of addition is controlled to maintain the temperature of the solution at 40° C. due to the exothermic nature of the reaction. After 30 minutes, the reaction is complete (based on gas chromatographic analysis) and the ethanol and water solvents are removed on a rotary evaporator. Toluene is added to azeotropically remove water. The light tan-colored oil which results in then stirred at 0° C.–10° C. in 40 ml of absolute ether and 12 ml of ethanol. Powdered NaOH (2.4 g, 0.06 mole) is added over 5 minutes and a white precipitate immediately forms. After 1 hour at 0° C.–10° C., the mixture is filtered of NaCl and the organic solvents removed on a rotary evaporator. A gas chromatographic trace of the final liquid product indicates 98.8 percent purity to the desired N,N-dimethyl-2,3-epoxypropyl carbamate.

The crude product (7.2 g, 99 percent) distills at 68° C. (0.25 mm Hg pressure) to give a water white liquid product of more than 99 percent purity.

EXAMPLE 3

Preparation of Bis-(2,3-Epoxypropyl) 1,4-Piperazinyl Dicarboxylate

A solution of epichlorohydrin carbonate (13.65 g, 0.1 mole) in 50 ml of absolute ethanol is stirred under a N$_2$ atmosphere in a 250-ml round-bottom flask and heated to 60° C. (oil bath). To this, a solution of anhydrous piperazine (4.3 g, 0.05 mole) in 20 ml of absolute ethanol is added dropwise over 30 minutes. Stirring and heating are continued for 4 hours. An infrared spectrum of the reaction solution shows little or no carbonyl (C=O) absorption at 1790 cm$^{-1}$ due to the carbonate reactant, and a broad carbonyl absorption at 1690–1700 cm$^{-1}$ due to carbamate-containing product. The solution is then cooled to 0° C. to 10° C. in an ice bath and powdered NaOH (4.4 g, 0.11 mole) is added with vigorous stirring. Within 5 to 10 minutes a thick, white precipitate forms (NaCl) which after 30 minutes is filtered off and washed with 10 ml of absolute ethanol, then 10 ml of absolute ether. Solvent is removed using a rotary evaporator with the product solution immersed in a water bath at no greater than 40° C. Upon removal of the solvent, a straw yellow, viscous oil is left that is soluble in acetone, trichloromethane, methanol and ethanol, and insoluble in ether. A nuclear magnetic resonance spectrum of the product oil in CDCl$_3$ shows the oil to contain approximately 90–95 percent epoxide-containing product in the form of the diglycidyl ester of piperazine dicarboxylate.

Upon standing for 5 days at room temperature, the oil crystallized to a solid mass and is stirred in a solution of absolute ether:absolute ethanol (6:1) and filtered to give 6.44 g (45 percent) pure diglycidyl ester of piperazine dicarboxylate (M.P. 88° C., elemental analysis: theoretical 50.35 percent C, 6.34 percent H, 9.79 percent N; found 50.36 percent C, 6.73 percent H, 9.68 percent N). Evaporation of the ethanol/ether solution gives 7.3 g (51 percent) straw yellow oil consisting primarily of epoxide terminated monomers and oligomers of the diglycidyl ester of piperazine dicarboxylate.

EXAMPLE 4

Preparation of (3-Chloro-2-hydroxy)propyl Piperidinyl Carboxylate

Distilled piperidine (4.25 g, 0.05 mole) in 25 ml of acetonitrile is added dropwise over a 30-minute period via a graduated addition funnel to a vigorously stirring solution of distilled epicarbonate of more than 99 percent purity (MW 136, 6.8 g, 0.05 mole) in 50 ml of acetonitrile. When conversion to 1,2-dichlorohydrin product is more than 98.5 percent complete, the reaction is terminated and 50 ml of diethyl ether is added, resulting in the immediate precipitation of piperidine-HCl complex. The salt complex is then removed by filtering through a medium sintered glass funnel. The filtrate is then rotary evaporated without heat leaving a crude, yellow viscous oil product. The crude oil is dissolved in anhydrous diethyl ether (100 ml), washed with a 5 percent solution of aqueous HCl, dried over magnesium sulfate and then rotary evaporated to remove the solvent. The resulting chlorohydrin of piperidine is obtained as a clear colorless oil (more than 99 percent purity) in approximately 80 percent yield.

EXAMPLE 5

Preparation of (3-Chloro-2-hydroxy)propyl N,N-piperazinyl Dicarboxylate

A solution of epichlorohydrin carbonate distilled to more than 99 percent purity (MW 136.5, 20.97 g, 0.15 mole) in 100 ml of acetonitrile along with sodium bicarbonate is stirred in an air atmosphere in a 250-ml round-bottom flask at about 20° C. A solution of anhydrous, sublimed piperazine (MW 86.0, 6.39 g, 0.074 mole) in 50 ml of absolute EtOH is added dropwise at a rate of 4 drops/min. The reaction is continued for 3 days at about 20° C. Isolation of the (3-chloro-2-hydroxy)propyl N,N-piperazinyl dicarboxylate is accomplished by first removiong the NaHCO$_3$ by filtering through a medium sintered funnel, then removing the reaction solvent on a rotary evaporator. The concentrated reaction product containing (3-chloro-2-hydroxy)propyl N,N-piperazinyl dicarboxylate and excess epichlorohydrin is placed on a silica column (60–200 mesh) and eluted with a 50/50 solution of CH$_2$Cl$_2$/CCl$_4$. The epichlorohydrin passes through the column leaving behind the (3-chloro-2-hydroxy)propyl N,N-piperazinyl dicarboxylate product. The product is then removed from the column by elution with ethanol. After removal of ethanol via rotary evaporation, a white solid immediately forms. The solid is identified by infrared, $^1$H nuclear magnetic resonance and elemental analysis as the (3-chloro-2-hydroxy)propyl N,N-piperazinyl dicarboxylate which has a melting point of 105° C.

What is claimed is:

1. A compound which comprises one or more 3-halo-2-hydroxyalkyl carbamate moieties wherein the carbamate nitrogen is tertiary.

2. The compound of claim 1 wherein the carbamate nitrogen atom is substituted by a alicyclic or aliphatic moiety or is part of a heterocyclic ring, wherein the heterocyclic ring can contain an oxygen or sulfur atom or may contain a tertiary nitrogen atom of a 3-halo-2-hydroxyalkyl carbamate moiety; or wherein two or more 3-halo-2-hydroxyalkyl carbamates are linked by an aliphatic or alicyclic moiety.

3. A compound of claim 2 which is a 3-halo-2-hydroxyalkyl carbamate and poly-(3-halo-2-hydroxyalkyl)polycarbamates.

4. A compound of claim 3 wherein the 3-halo-2-hydroxylalkyl carbamate is a dialiphatic or dialicyclic carbamate or a 3-halo-2-hydroxyalkyl cycloalkylene carbamate, or the poly-(3-halo-2-hydroxyalkyl)polycarbamate is a poly-(2,3-epoxyalkyl) N-aliphatic or N-alicyclic alkylene polycarbamate, or a bis-(2,3-epoxyalkyl) 1,4-piperazinyl dicarboxylate.

5. A compound of claim 4 which is poly-(3-halo-2-hydroxyalkyl) N-aliphatic or N-alicyclic alkylene polycarbamate or bis-(3-halo-2-hydroxyalkyl) 1,4-piperazinyl dicarboxylate.

6. A compound of claim 4 which is a 3-halo-2-hydroxypropyl dialiphatic or dialicyclic carbamate, a (3-halo-2-hydroxypropyl)alkylene carbamate, a poly-(3-halo-2-hydroxypropyl) N-aliphatic or N-alicyclic alkylene polycarbamate, or a bis-(3-halo-2-hydroxypropyl) 1,4-piperazinyl dicarboxylate.

7. A compound of claim 8 which is a poly-(3-halo-2-hydroxypropyl) N-aliphatic or N-alicyclic alkylene polycarbamate, or bis-(3-halo-2-hydroxypropyl) 1,4-piperazinyl dicarboxylate.

8. A 3-halo-2-hydroxyalkyl carbamate of claim 4 which corresponds to the formula

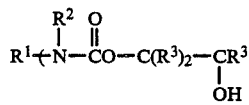 or 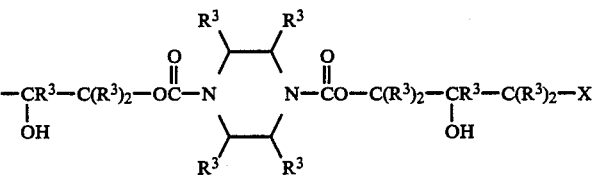

wherein
R$^1$ is separately in each occurrence an n valent aliphatic or cycloaliphatic hydrocarbon;
R$^2$ is separately in each occurrence an aliphatic or cycloaliphatic moiety;
R$^3$ is separately in each occurrence hydrogen or an aliphatic moiety;
X is I, Cl or Br; and
n is an integer of 1 to 6;
wherein R$^1$ and R$^2$ may be joined to form a cycloalkylene moiety which can contain the heteroatoms O, N or S.

9. The composition of claim 8 wherein the 3-halo-2-hydroxyalkyl carbamate is a 3-halo-hydroxyalkyl dialiphatic or dialicyclic carbamate which corresponds to the formula $$R^1-N(R^2)-CO-C(R^3)_2-CR^3(OH)-C(R^3)_2-X;$$

a poly-(3-halo-2-hydroxyalkyl) N-aliphatic or N-alicyclic alkylene polycarbamate which corresponds to the formula $$R^4\!\!-\!\!(N(R^2)-CO-C(R^3)_2-CR^3(OH)-C(R^3)_2-X)_p;$$

a 3-halo-2-hydroxyalkyl cycloalkylene carbamate which corresponds to the formula $$R^5\!\!\frown\!\!N-CO-C(R^3)_2-CR^3(OH)-C(R^3)_2-X;$$

or a bis-(3-halo-2-hydroxyalkyl) 1,4-piperazinyl dicarboxylate which corresponds to the formula $$X-C(R^3)_2-CR^3(OH)-C(R^3)_2-OC(O)-N[\!(CR^3_2)_2\!]N-CO-C(R^3)_2-CR^3(OH)-C(R^3)_2-X$$

wherein
- $R^1$ is separately in each occurrence an aliphatic or cycloaliphatic radical;
- $R^2$ is separately in each occurrence an aliphatic or cycloaliphatic radical;
- $R^3$ is separately in each occurrence hydrogen or an aliphatic radical;
- $R^4$ is a p valent aliphatic or cycloaliphatic hydrocarbon;
- $R^5$ is an alkylene radical which can contain a heteroatom of O, S or N which together with the carbamate nitrogen atom forms an aliphatic heterocyclic ring;
- X is I, Cl or Br; and
- p is an integer of between 2 and 6, inclusive.

10. The 3-halo-2-hydroxyalkyl carbamates of claim 9 wherein
- $R^1$ is a $C_{1-20}$ aliphatic or $C_{3-20}$ cycloaliphatic radical;
- $R^2$ is a $C_{1-20}$ aliphatic or $C_{3-20}$ cycloaliphatic radical;
- $R^3$ is hydrogen or a $C_{1-20}$ aliphatic radical;
- $R^4$ is a p valent $C_{1-20}$ aliphatic or $C_{3-20}$ cycloaliphatic hydrocarbon radical;

$$R^5\!\!\frown\!\!N-$$

forms a piperidine, a pyrrolidine, oxazine, imidazolidine, morpholine, ethylenimine, or 3-pyrroline or perhydro-1,3-thiazine ring;
- X is Cl or Br; and
- p is the integer 2 or 3.

11. The 3-halo-2-hydroxyalkyl carbamate of claim 10 wherein
- $R^1$ is $C_{1-20}$ alkyl;
- $R^2$ is $C_{1-20}$ alkyl;
- $R^3$ is hydrogen or $C_{1-20}$ alkyl;
- $R^4$ is p valent $C_{1-20}$ alkyl radical;

$$R^5\!\!\frown\!\!N-$$

forms a piperidine, pyrrolidine, oxazine, or morpholine heterocyclic ring;
- X is Cl; and
- p is 2.

12. The 3-halo-2-hydroxyalkyl carbamates of claim 11 wherein
- $R^1$ is $C_{1-10}$ alkyl;
- $R^2$ is $C_{1-10}$ alkyl;
- $R^3$ is hydrogen or $C_{1-3}$ alkyl;
- $R^4$ is $C_{1-10}$ alkyl; and $$R^5\!\!\frown\!\!N-$$

forms a pyrrolidine or piperidine ring.

13. The 3-halo-2-hydroxyalkyl carbamate of claim 12 wherein $R^3$ is hydrogen.

14. A composition which comprises the product of the process which comprises contacting an epihalohydrin carbonate with a secondary amine-containing compound wherein the secondary amine has a pKa at which the secondary amine will react with the epihalohydrin carbonate and will not catalyze the formation of unwanted by-products, in a polar organic solvent under conditions such that a 3-halo-2-hydroxyalkyl carbamate, wherein the carbamate nitrogen is tertiary, is prepared.

15. The composition of claim 14 wherein the secondary amine is an aliphatic secondary amine, an aliphatic poly secondary amine, a heterocyclic secondary amine or piperazine.

16. The composition of claim 15 wherein the secondary amine corresponds to the formula $$R^1\!\!-\!\!(N(R^2)-H)_n$$

or

-continued

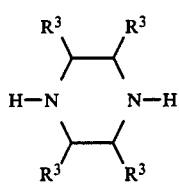

and the epihalohydrin carbonate corresponds to the formula

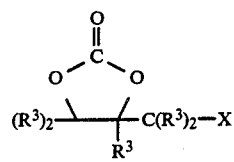

wherein $R^1$ is separately in each occurrence an n valent aliphatic or cycloaliphatic hydrocarbon;

$R^2$ is separately in each occurrence an aliphatic or cycloaliphatic moiety;

$R^3$ is hydrogen or an aliphatic radical;

X is I, Cl or Br; and n is an integer of 1 to 6;

wherein $R^1$ and $R^2$ may be joined to form a cycloalkylene moiety which can contain the heteroatoms O, N or S.

17. The composition of claim 16 wherein the amine is an aliphatic secondary amine which corresponds to the formula

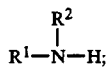

a heterocyclic secondary amine which corresponds to the formula

an aliphatic poly secondary amine which corresponds to the formula

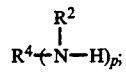

or piperazine which corresponds to the formula

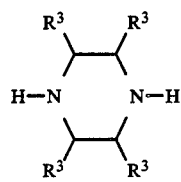

wherein $R^1$ is separately in each occurrence an aliphatic or cycloaliphatic radical;

$R^2$ is separately in each occurrence an aliphatic or cycloaliphatic radical;

$R^3$ is separately in each occurrence hydrogen or an aliphatic radical;

$R^4$ is a p valent aliphatic or cycloaliphatic hydrocarbon;

$R^5$ is an alkylene radical which can contain a heteroatom of O, S or N which together with the nitrogen forms an aliphatic heterocyclic ring; and p is an integer between 2 and 6, inclusive.

* * * * *